(12) United States Patent
Grichnik

(10) Patent No.: US 7,415,143 B2
(45) Date of Patent: Aug. 19, 2008

(54) METHODS AND SYSTEMS FOR THE DETECTION OF MALIGNANT MELANOMA

(75) Inventor: James J. Grichnik, Chapel Hill, NC (US)

(73) Assignee: Duke University, Durham, NC (US)

( * ) Notice: Subject to any disclaimer, the term of this patent is extended or adjusted under 35 U.S.C. 154(b) by 647 days.

(21) Appl. No.: 10/858,941

(22) Filed: Jun. 2, 2004

(65) Prior Publication Data

US 2005/0228264 A1 Oct. 13, 2005

Related U.S. Application Data

(60) Provisional application No. 60/561,570, filed on Apr. 13, 2004.

(51) Int. Cl.
*G06K 9/00* (2006.01)

(52) U.S. Cl. .................. 382/128; 382/172; 600/306

(58) Field of Classification Search ............. 382/100, 382/128, 129, 130, 131–133, 199, 203, 219, 382/224, 254, 274, 275, 285, 312, 154, 162, 382/168, 172, 232, 276, 305; 600/306, 476; 356/369; 378/18, 29
See application file for complete search history.

(56) References Cited

U.S. PATENT DOCUMENTS

| 5,836,872 | A  | * | 11/1998 | Kenet et al. | 600/306 |
| 6,032,071 | A  | * | 2/2000  | Binder       | 600/476 |
| 6,208,749 | B1 | * | 3/2001  | Gutkowicz-Krusin et al. | 382/128 |
| 6,215,893 | B1 | * | 4/2001  | Leshem et al. | 382/128 |
| 7,006,223 | B2 | * | 2/2006  | Mullani      | 356/369 |
| 7,162,063 | B1 | * | 1/2007  | Craine et al. | 382/128 |

OTHER PUBLICATIONS

Kittler, H. et al., "Follow-up of melanocytic skin lesions with digital epiluminescence microscopy: patterns of modifications observed in early melanoma, atypical nevi, and common nevi," *J Am Acad Dermatol* 43(3):467-476 (2000).

Masri, G. et al, "Screening and surveillance of patients at high risk for malignant melanoma result in detection of earlier disease," *J Am Acad Dermatol* 22(6):1042-1048 (1990).

* cited by examiner

*Primary Examiner*—Seyed Azarian
(74) *Attorney, Agent, or Firm*—Medlen & Carroll, LLP

(57) ABSTRACT

The present invention relates to the detection of malignant melanoma. In particular, the present invention relates to systems and methods for the early detection of cancerous lesions.

30 Claims, 1 Drawing Sheet

METHODS AND SYSTEMS FOR THE DETECTION OF MALIGNANT MELANOMA

This application claims priority to provisional patent application Ser. No. 60/561,570, filed on Apr. 13, 2004, which is herein incorporated by reference in its entirety.

FIELD OF THE INVENTION

The present invention relates to the detection of malignant melanoma. In particular, the present invention relates to systems and methods for the early detection of cancerous lesions.

BACKGROUND OF THE INVENTION

Melanoma is a malignant tumor of melanocytes, cells that are derived from the neural crest. Although most melanomas arise in the skin, they may also arise from mucosal surfaces or at other sites to which neural crest cells migrate. Melanoma occurs predominantly in adults, and more than half of the cases arise in apparently normal areas of the skin. Early signs of malignant melanoma in a mole include darker or variable discoloration, itching, or an increase in size. Ulceration or bleeding are later signs. Melanoma can arise from any site on the skin surface.

Melanoma is generally diagnosed by a biopsy, preferably by local excision. Specimens are then examined by a pathologist to allow for microstaging. Studies show that distinguishing between benign pigmented lesions and early melanomas can be difficult, and even experienced dermatopathologists can have differing opinions.

Prognosis is affected by clinical and histological factors and by anatomic location of the lesion. Thickness and/or level of invasion of the melanoma, mitotic index, presence of tumor infiltrating lymphocytes, number of regional lymph nodes involved, and ulceration affect the prognosis. Patients who are younger, female, and who have melanomas on the extremities generally have a better prognosis.

If not treated, most melanomas eventually spread to other parts of the body. Melanomas rarely disappear without treatment (spontaneous regression) once they have spread. Metastatic melanoma usually cannot be cured. Early detection and removal of primary melanomas before they metastasize can prevent death from melanoma.

What is needed in the art are better methods for the early detection of melanoma. Preferred methods are non-invasive and able to detect melanomas before metastasis.

SUMMARY OF THE INVENTION

The present invention relates to the detection of malignant melanoma. In particular, the present invention relates to systems and methods for the early detection of cancerous lesions.

Accordingly, in some embodiments, the present invention provides a method, comprising the steps of: providing at least one initial body image (e.g., photograph or digital image) from a subject; and at least one follow up body image from the subject, wherein the follow up body image is taken at a later time than the initial body image; and comparing the initial body image and the follow up body image to identify moles or lesions that are both nonuniform and changed. In some embodiments, the body images are in a 2 or 3 dimensional format (e.g., obtained through cameras or scanning devices). In some embodiments, the method further comprises the step of providing a diagnosis of the presence or absence of melanoma in the subject. In other embodiments, the method further comprises the step of providing a level of the subject's risk of developing melanoma. In some embodiments, moles or lesions that are both nonuniform and changed are indicative of potential melanoma. In other embodiments, moles or lesions that are both nonuniform and changed are indicative of dysplastic nevus with severe cytologic atypia. The present invention is not limited to a particular interval of follow up images. However, in certain preferred embodiments, the at least one follow up body image is taken once every 12, and preferably once every 6 months. In some embodiments, the method further comprises providing at least one initial dermoscopy image (or image derived from a technique that provides similar information—e.g., direct scanning followed by computer assessment to simulate information obtained from dermoscopy) and at least one follow up dermoscopy image. In some embodiments, the at least one initial dermoscopy image and the at least one follow up dermoscopy image are compared to identify moles or lesions that are both nonuniform and changed. In some embodiments, the initial and follow up body images are compared by at least one dermatologist. In other embodiments, the initial and follow up body image are compared by a computer processor and computer software. In some embodiments, the computer software and the computer processor provide a diagnosis of the presence or absence of melanoma to the subject. In certain embodiments, the method further comprises the step of excising the moles or lesions found to be both nonuniform and changed. In some embodiments, a set of control body images is provided, wherein the control body images illustrate changed and nonchanged as well as uniform and nonuniform moles or lesions.

The present invention further provides a system an apparatus configured for the comparison of one or more initial body images with one or more follow up body images to identify moles or lesions that are both nonuniform and changed. In some embodiments, the apparatus comprises a computer processor and computer software. In some embodiments, the apparatus is further configured to provide a diagnosis of melanoma for the moles or lesions identified as both nonuniform and changed. In other embodiments, the apparatus is further configured to provide a level of risk of melanoma being present in the moles or lesions. In some embodiments, the at least one follow up body image is taken once every 12, and preferably once every 6 months. In some embodiments, at least one initial dermoscopy image and at least one follow up dermoscopy image are provided. In some embodiments, the apparatus is further configured for comparing the at least one initial dermoscopy image and the at least one follow up dermoscopy image to identify moles or lesions that are both nonuniform and changed. In some preferred embodiments, the system further comprises a set of control body images, wherein the control body images illustrate changed and nonchanged as well as uniform and nonuniform moles or lesions.

DEFINITIONS

Figure 1:
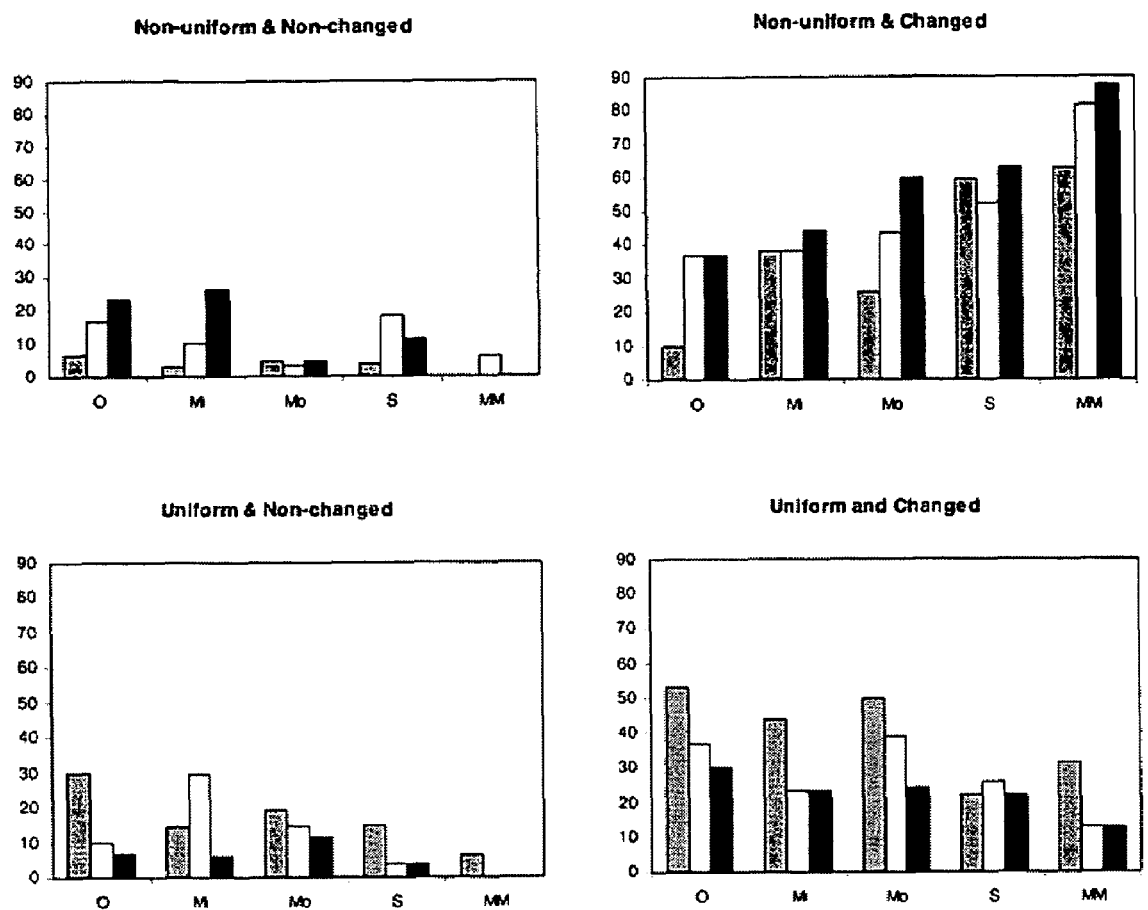
FIG. 1 shows a chart of the analysis of moles using the methods of some embodiments of the present invention.

As used herein, the term "nevi" or "mole" refers to a typically noncancerous skin growth made up of cells (melanocytes or nevus cells) that produce color (pigment). Moles can appear anywhere on the skin, alone or in groups.

As used herein, the term "lesion" refers to a mole that is under examination (e.g., is suspected of being cancerous or has been diagnosed as cancerous) and may or may not be cancerous. In some embodiments, "lesion" is used interchangeably with "mole" or "nevi."

As used herein, the term "melanoma" or "malignant melanoma" refers to a serious form of skin cancer that may affect the skin only or may spread (metastasize) through the blood or lymph systems to organs and bones. Melanoma can develop in an existing mole or other mark on the skin or on unmarked skin.

As used herein, the term "metastatic melanoma" refers to melanoma that has spread to other tissues or organs.

As used herein, the term "nonuniform" refers to the deviation of one or more features in a lesion from uniformity. In some preferred embodiments, the determination of uniformity is based on the establishment of a center (origin) and an edge (border) where the lesion interfaces with the normal skin. In some embodiments, the center is determined by a clinical assessment, while in other embodiments it is determined by a computer algorithm (e.g., using any suitable system, including methods that assess mathematical average distances from a plurality of points on the border across the lesion). In other embodiments, the center is weighted based on lesion qualities and/or prior data. Examples of "nonuniformity" include, but are not limited to, shifting of the center to the center of a portion of the lesion thought to represent the original clonal population (for instance exclusion of distinct secondary subpopulations from the overall assessment of center) and/or shifting of the center compared to prior images (e.g., due to prior images indicating a more precise location). In some embodiments, the edge is determined by a clinical assessment, while in other embodiments it is determined by a computer algorithm (e.g., by detecting changes in color, texture, etc.). In some embodiments, the edge is defined as the location where the detectable lesion (e.g., clinically, microscopically, or computer detection) meets normal skin.

In some embodiments, a lesion is considered "uniform" if the gradient of features from the center to the edge is consistent throughout the entire lesion (full 360°). This does not require that the edges be symmetrical as long as the relative gradient of features is similar from the center to the edge. A lesion not fulfilling these criteria is considered "non-uniform". In some embodiments, the threshold for when a lesion is uniform or non-uniform is decided by clinical assessment or by computer algorithm. For example, clinical and computer assessments start in the center of a lesion and look to the edges of the lesion through the full 360°. The gradient of features (including but not limited to, reflectance, absorbance, color features, intensities, forms, and/or patterns) from the center to the edge are averaged throughout the full 360°. The lesion is then evaluated in slices from the center to the edge (e.g., like pieces of a pie). These pieces may range from 1-120° increments. The deviation of the gradient of features from the center (tip of the slice) to the edge (crust of the slice) is determined by comparing this increment with the average. Deviations exceeding a determined threshold place the lesion in the non-uniform category. In other embodiments, levels of non-uniformity are determined based on a scale of deviation thresholds. Thresholds may be selected based on averages determined from multiple lesions (e.g., from an individual or population) correlated to clinical outcome (e.g., a threshold is selected as the level of non-uniformity that statistically correlates to melanoma).

As used herein, the term "change" refers to an apparent increase of area of a lesion or new lesion, or the development of a new lesion feature associated with the appearance of melanoma within a mole; specifically, nonuniform expansion of pigment from one edge of the lesion into adjacent normal skin or the dramatic appearance of new nonuniform pigmentation. In some embodiments, a changed lesion exhibits at least a 20% increase in area. In other embodiments, a changed lesion exhibits at least a 40%, more preferably at least a 60% and even more preferably at least an 80% or 100% increase in area.

As used herein, the term "unchanged" refers to a lesion that does not exhibit characteristics of change.

As used herein, the term "body image" refers to any photograph or image or collection of photographs or images that can be interpreted by a human or a machine (e.g., computer) that show moles or lesions on a subject's body. In preferred embodiments, the photographs or images show all or substantially all of the moles or lesions present on the subject (i.e., "whole body" photographs or images). In certain embodiments, the photographs or images show only moles or lesions that differ from a subject's normal moles or lesions or show one or more characteristics of cancerous growths.

As used herein, the term "dermoscopy" refers to a body imaging technique that involves analysis with the use of, for example, oil or cross polarized light to limit surface reflectance. In general, dermoscopy images cover a small area (e.g., several cm) of skin, although the term is not limited to images covering only a small area of skin. The present invention contemplates larger (e.g., whole body) dermoscopy.

As used herein, the term "initial body image" refers to a photograph or image that is taken at an initial or first time point.

As used herein, the term "follow up body image" refers to a photograph or image that is taken after an initial photograph or image. In some embodiments, follow up photographs or images are taken at regular time intervals (e.g., every 3-24 months), although the present invention is not limited to a particular time interval.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

DESCRIPTION OF THE INVENTION

Early melanoma detection poses several problems. First, whereas advanced melanomas are obvious, early melanoma lesions are often subtle (Menzies et al., Arch Dermatol 2001; 137:1583-9). Second, dysplastic (atypical) nevi may demonstrate many of the characteristics recognized as risks for melanoma (Friedman et al., CA Cancer J Clin 1985; 35:130-51) (ABCD's, asymmetry, border irregularity, color variation, and diameter>6 mm), but they are nonmalignant and vastly outnumber actual melanomas. Third, definitive markers to firmly establish a malignant diagnosis in the absence of metastatic disease are lacking (Swerlik et al., Arch Dermatol 1996; 132:881-4). Thus, it is possible that some early melanomas are inadvertently diagnosed as benign and vice versa. Fourth, on an annual basis, each melanoma must be detected in a background of approximately 200,000 benign nevi (Sagebiel et al., Skin Cancer Found J 1996; 14:38-40).

Melanoma detection can be improved through various approaches. One area is patient education. A patient familiar with the risk of melanoma may detect the presence of a mole displaying concerning features, prompting earlier medical intervention. Another approach, total body skin examination, may reveal the presence of a mole with concerning features. Often, this mole is different from the patient's average mole (Grob and Bonerandi, Arch Dermatol 1998; 134:103-4). Dermoscopy may be used to visualize patterns to help discriminate benign from malignant melanocytic lesions (Steiner et al., J Am Acad Dermatol 1987; 17:571-83; Steiner et al., J Am Acad Dermatol 1987; 17:584-91; Kenet et al., Arch Dermatol 1993; 129:157-74; Pehamberger et al., J Invest Dermatol 1993; 100(Suppl):356-62S). In addition, regular surveillance may allow for the detection of an early melanoma, before it comes to a patient's attention, in those at high risk (Rivers et al., Cancer 1990; 65:1232-6). Surveillance may incorporate the use of dermoscopic or total body photographic images in an effort to identify changes worrisome for melanoma (Masri et al., J Am Acad Dermatol 1990; 22:1042-8; Rivers et al., Cancer 1990; 65:1232-6; Kittler et al., J Am Acad Dermatol 2000; 43:467-76; Grichnik, Melanoma Lett 1998; 16:3-4; Kelly et al., Med J Aust 1997; 167:191-4; Tiersten et al., J Dermatol Surg Oncol 1991; 17:44-8; Halpern et al., J Invest Dermatol 1993; 100(Suppl):346-9S; Mackie et al., Lancet 1993; 341:1618-20; Marghoob et al., Arch Dermatol 1994; 130: 993-8; Rhodes, J Am Acad Dermatol 1998; 39:262-7). A common goal for these approaches is to identify and excise potentially malignant lesions while minimizing unnecessary biopsies of benign lesions. However, these approaches still miss many early melanomas that do not meet the criteria for removal until they are in an advanced stage. The random removal of dysplastic nevi is not an effective approach for melanoma detection (Kelly et al., supra).

Even with dermoscopy, melanomas in their early stages can be quite difficult to detect. Traditional features correlated with malignancy such as atypical pigment network, pseudopods, blue-white veil, multiple colors, or irregular dots/globules may not be present (Menzies et al., Arch Dermatol 1996; 132:1178-82). For some of these lesions, change may be the only feature suggesting malignancy (Menzies et al., Arch Dermatol 2001; 137:1583-9). As the lesions grow, traditional dermoscopic features associated with malignancy may become apparent (Kittler et al., supra). Benign nevi can also be noted to grow. In general, these lesions enlarge in a symmetric manner (Kittler et al., supra).

Given the potential lack of traditional malignant dermoscopic features on early melanoma lesions, it is important to consider other criteria that might be useful in discriminating early malignant lesions. The present invention is not limited to a particular mechanism. Indeed, an understanding of the mechanism of the present invention is not necessary to practice the present invention. Nonetheless, it is contemplated that benign nevi are caused by mild defects in growth regulation whereas melanomas are caused by critical defects in growth regulation. A secondary defect could also occur in a benign neoplasm transforming a subclone of cells to a malignant tumor. Following this line of reasoning, benign nevi should be manifested by uniform growth with eventual stabilization of the proliferation and malignant neoplasms start out in a uniform manner, but with time differentiate themselves from benign lesions by the development of nonuniform growth patterns (because of the progressive loss of regulatory controls) and failure to stabilize growth. Therefore, it is contemplated that nonuniformity is a useful dermoscopic feature for the evaluation of early lesions.

Dermoscopic change has been shown to aid in the identification of early melanomas. However, this approach is limited to specific lesions chosen for photography (Menzies et al., supra; Kittler et al., supra). In contrast, total body photography allows for an assessment of change to be made for any mole during a follow up visit, particularly newly developed lesions.

Accordingly, in some embodiments, the present invention provides methods that overcome the shortcomings of the existing detection methods. For example, in some embodiments, the methods of the present invention utilize an analysis of the combination of dermoscopy and photographs or images or all or portions of the body for identification of nonuniform surface detail and growth. Experiments conducted during the course of development of the present invention used photographic archives of lesions removed during follow-up of patients with photographs for which dermoscopic and clinical photos were available. Experiments conducted during the course of development of the present invention identified that dermoscopic nonuniformity and change suggestive of growth as determined from total body photos discriminates a subset of lesions that are at high risk for melanoma.

The present invention provides methods of identifying lesions that are at high risk of becoming malignant. The present invention provides systems employing an algorithm that uses dermoscopic nonuniformity and growth compared with baseline body photos or similar standards to identify the majority of melanomas. Body photos or images (e.g., whole body photographs or images) and/or dermoscopic images are reviewed over time and moles or lesions that are both nonuniform and changed in size are identified as potential melanomas. In some embodiments, body photographs covering a portion of the body are used to determine changed lesions. In some embodiments, higher resolution images (e.g., including, but not limited to, dermoscopy images) of lesions that are changed are then obtained for use in the determination of uniformity. In some embodiments, the whole or partial body photographs are used for determination of both change and uniformity. In other embodiments, all images are taken at a high resolution and used in all aspects of analysis of a lesion.

In some preferred embodiments, images are obtained at time intervals (e.g., regular or irregular intervals). The present invention is not limited to a particular time interval. In some embodiments, the time intervals range from once every several months to once every several years. In preferred embodiments, images are obtained at regular or semi-regular intervals ranging from once every 3 months to once every 12 months.

In some embodiments, the methods of the present invention find use in the generation of risk categories for a given lesion. For example, in some embodiments, lesions are graded on a scale ranging from low risk of the lesion being melanoma to a high risk. In some embodiments, the scale is numerical (e.g., 1 to 10, with 1 being low risk and 10 being high risk). In other embodiments, the methods of the present invention provide a diagnosis (which need not be limited to 100% sensitivity or accuracy) of the presence of absence of melanoma in a subject.

Thus, the present invention provides systems and methods for the early detection of melanomas. The early removal of melanoma (e.g., before metastasis) greatly increases the likelihood of cancer free survival. The present invention is not limited by the nature of the imaging technique used or by the amount of body surface (e.g., a portion of vs. the whole body) analyzed.

In some embodiments, the images are reviewed by analysis clinicians (e.g., dermatologists). In some embodiments, more than one (e.g., two or more) analysis clinicians review each image before a mole or lesion is identified as a potential melanoma. The methods of the present invention further find use in monitoring individuals that have been diagnosed as having melanoma for a second primary melanoma or recurrence of the original melanoma (e.g., at the same or different sites on the body).

I. Automation

In some embodiments, the review and analysis of body photographs or images is automated (e.g., by using computer software and a computer processor). In some embodiments, the computer software generates diagnostic or predictive information for use by the treating clinician. In some embodiments, the software and computer systems of the present invention are configured for performing all of the necessary steps of the diagnostic methods described herein.

A. Analysis Systems and Apparatuses

In some embodiments, the computer systems are configured for the collection of images. In some embodiments, images are obtained, for example as digital images. In other embodiments, non-digital photographs are taken and then they are transferred to a digital format (e.g., by scanning). In yet other embodiments, the computer system analyzes photographs/images directly. In some embodiments, multidimensional images (e.g., 2D or 3D images) are obtained using a skin surface scanner.

In certain preferred embodiments, the computer systems store control images for use in the determination of the level of change or uniformity of a subject's moles or lesions. In some embodiments, the control images are obtained from heterologous subjects or pools of heterologous subjects. In other embodiments, the images comprise normal moles from the subject being analyzed. In such embodiments, the software uses the subject's normal mole pattern to aid in the identification of abnormal moles or lesions (e.g., by comparing the subject's normal pool of moles to lesions suspected of being cancerous). In certain embodiments, the software stores a series of images from the same subject taken over time (e.g., at particular intervals) to use in the determination of change.

In some embodiments utilizing control or reference images, the software compares the control images or stored prior images to lesions or moles under examination. The software then computes the deviation of one or more parameters (e.g., uniformity) of the lesion under examination to the reference image. In other embodiments, the software compares the lesion under examination to initial images of the same lesion. In preferred embodiments, the software first compares the lesion under examination to the initial image of the same lesion. Images deviating from the initial image are then compared to the reference image to aid in the determination of a diagnosis.

B. Determination of Non-Uniformity and Change

Any number of parameters of the lesion may be used by the software in the determination of uniformity or nonuniformity of a given lesion. In some embodiments, uniformity is based on the concept that a benign mole or melanoma originates in the skin from a focal defect (this does not exclude the role that systemic factors, genetics, environment, and circulating cells play in melanoma and mole development). The present invention is not limited to a particular mechanism. Indeed, an understanding of the mechanism is not necessary to practice the present invention. Nonetheless, it is contemplated that this defect is presumed to be a mutated melanocytic cell (precursor cell or melanocyte).

For both benign and malignant lesions growth starts focally and then expands outward. Malignant lesions lack tight regulatory controls. Thus, as the lesion grows away from the origin, the cells may change their behavior (e.g., due to, but not limited to, additional mutations or changes in cellular differentiation). The relative independence of the malignant cells allows for cells expanding in one area of the lesion to demonstrate features different from cells on the other side (or other part) of the lesion. This may be due to, but not limited to, altered rates of pigment production, altered types of pigment, altered growth rates, altered locations of growth, and different clones of cells (survival of the fittest).

For the prototypical benign lesion, as the cells expand from the center they will retain similar regulatory controls. Cells may demonstrate different features as they expand a certain distance from the center (possibly due to, but not limited to, changes in cytokine levels, changes in differentiation, changes in proliferate potential), but these features are consistently maintained circumferentially around the lesion as the cells expand outward.

In some preferred embodiments, the determination of uniformity is based on the establishment of a center (origin) and an edge (border) where the lesion interfaces with the normal skin. In some embodiments, the center is determined by a clinical assessment, while in other embodiments it is determined by a computer algorithm. In other embodiments, the center is weighted based on lesion qualities and/or prior data. Examples of nonuniformity include, but are not limited to, shifting of the center to the center of a portion of the lesion thought to represent the original clonal population (for instance exclusion of distinct secondary subpopulations from the overall assessment of center) and/or shifting of the center due to prior images indicating a more precise location.

In some embodiments, the edge is determined by a clinical assessment, while in other embodiments it is determined by a computer algorithm. In some embodiments, the edge is defined as the location where the detectable lesion (e.g., clinically, microscopically, or computer detection) meets normal skin.

In some embodiments, a lesion is considered uniform if the gradient of features from the center to the edge is consistent throughout the entire lesion (full 360°). This does not require that the edges be symmetrical as long as the relative gradient of features is similar from the center to the edge. A lesion not fulfilling these criteria is considered non-uniform. In some embodiments, the threshold for when a lesion is uniform or non-uniform is decided by clinical assessment or by computer algorithm. In some embodiments, levels of non-uniformity are used to further grade the risk of a lesion. Clinical and computer assessments start in the center of a lesion and look to the edges of the lesion through the full 360°. The gradient of features (including but not limited to, reflectance, absorbance, color features, intensities, forms, and/or patterns) from the center to the edge are averaged throughout the full 360°. The lesion is then evaluated in slices from the center to the edge (e.g., like pieces of a pie). These pieces may range from 1-120° increments. The deviation of the gradient of features from the center (tip of the slice) to the edge (crust of the slice) is determined by comparing this increment with the average. Deviations exceeding a determined threshold place the lesion in the non-uniform category. In other embodiments, levels of non-uniformity are determined based on a scale of deviation thresholds. Thresholds may be selected based on averages determined from multiple lesions (e.g., from an individual or population) correlated to clinical outcome (e.g., a threshold is selected as the level of non-uniformity that statistically correlates to melanoma). In some embodiments, the results of analyses performed is used to optimize the parameters for diagnosis (See e.g., below section on research applications).

In preferred embodiments, the software further utilizes a change (e.g., greater than 20%, preferably greater than 40%, even more preferably greater than 60% and still more preferably greater than 80% or 100%) in size of a mole or lesion in the diagnosis of a lesion as a potential melanoma. In preferred embodiments, the presence of both change and nonuniformity is used in the determination of a lesion being a potential melanoma.

In certain embodiments, the software and computer systems of the present invention are further configured for the delivery of information (e.g., diagnostic or research information) to interested parties (e.g., subjects, clinicians and researchers). The automated delivery of information is discussed in greater detail below.

II. Delivery of Information

The methods of the present invention find use in a variety of patient care settings. In some embodiments, a computer-based analysis program is used to translate the raw data generated by the analysis of images (e.g., the presence or absence of a suspected melanoma) into data of predictive value for a treating clinician. The treating clinician can access the predictive data using any suitable means. Thus, in some preferred embodiments, the present invention provides the further benefit that the treating clinician, who is not likely to be trained in pathology or oncology, need not understand the raw data. The data is presented directly to the treating clinician in its most useful form. The clinician is then able to immediately utilize the information in order to optimize the care of the subject.

The present invention contemplates any method capable of receiving, processing, and transmitting the information to and from clinicians or computers conducting the assays, information provides, medical personal, and subjects. For example, in some embodiments of the present invention, an image is obtained by the primary care doctor or by the patient at home and submitted to an analysis service (e.g., lab at a medical facility, or computer analysis facility), located in any part of the world (e.g., in a country different than the country where the subject resides or where the information is ultimately used) to generate raw data. Once received by the analysis service, the images are processed and a result is generated (i.e., identification of moles or lesions suspected of being melanoma), specific for the diagnostic or prognostic information desired for the subject.

The profile data is then prepared in a format suitable for interpretation by a treating clinician (e.g., primary care doctor). For example, the prepared format may represent a diagnosis or risk assessment for the subject, along with recommendations for particular treatment options. The data may be displayed to the clinician by any suitable method. For example, in some embodiments, the analysis service generates a report that can be printed for the clinician (e.g., at the point of care) or displayed to the treating clinician on a computer monitor. In some embodiments, the report highlights the lesions of highest risk and/or provides a relative risk assessment based on an easy-to-interpret scoring system (e.g., a 1-5 ranking where 1 is clearly benign and 5 is clearly malignant).

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis (e.g., the same team of pathologists review all photos). The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results.

III. Research Applications

The present invention is not limited to diagnostic and prognostic applications. In other embodiments, the methods and systems of the present invention find use in research applications. For example, in some embodiments, data obtained using the methods and systems of the present invention is used to further optimize the parameters for identification of particular moles as potentially cancerous.

In other embodiments, the methods and systems of the present invention are used to monitor the efficacy of melanoma treatments (e.g., drugs, surgery, etc.). For example, the uniformity and change of a particular lesion can be monitored to test the effect of a drug or other intervention in clinical trials.

EXPERIMENTAL

The following examples are provided in order to demonstrate and further illustrate certain preferred embodiments and aspects of the present invention and are not to be construed as limiting the scope thereof.

Example

Early Detection of Melanoma

This example describes methods for the early detection of melanoma utilized in some embodiments of the present invention.

A. Materials And Methods

Data Set

All lesions suggestive of melanoma are removed on a patient's initial visit. None of these lesions are included in this set. Patients perceived as being at high risk (numerous clinically atypical [dysplastic] nevi or prior melanoma) are then photographed (high-resolution digital 3072×2048, 33 views) (MoleMapCD, DigitalDerm Inc) and followed up. A 4-step process is then undertaken that is efficient and used on all follow up visits. First, lesions that concern the patient are identified. Second, total body skin examination is undertaken to identify lesions with concerning clinical features or lesions appearing to deviate from the patient's average type(s) of mole(s). Third, dermoscopy is used for worrisome lesions identified during the first 2 steps. Fourth, all lesions for which there is any level of concern are compared with baseline photos. The great majority of these lesions are found to be stable and are not excised. Lesions with an element of clinical concern and demonstrated change are excised.

Thus, this set is comprised of worrisome lesions, from patients at high risk, of which the great majority demonstrated a change compared with the total body photos to the clinic physician. 526 patients with photos were followed up for an average of 2.4 years (range: 3 to 78 months) for a total of 1254 patient years. In total, 189 melanocytic lesions were removed during follow-up from 115 patients. The average follow up excision rate was 0.15 biopsies per patient year. The pathologic diagnoses of these lesions included 6 invasive melanomas, 15 in situ melanomas, and 28 dysplastic nevi with severe atypia (Table I). The original pathologic interpretation, used for patient care, was accepted as the correct diagnosis for all lesions.

TABLE I

Data compilation

| Diagnoses | All (including lesions with incomplete images) | Study set (complete image set available) |
| --- | --- | --- |
| Lesion total | 189 | 169 |
| Melanoma | 21 | 16 |
| Invasive (all <1.0 mm) | 6 | 5 |
| In situ | 15 | 11 |
| Dysplastic nevi | 130 | 123 |
| Severe cytologic atypia | 28 | 27 |
| Moderate cytologic Atypia | 65 | 62 |
| Mild cytologic atypia | 37 | 34 |
| Other | 38 | 30 |
| Spitz/Reed | 2 | 2 |
| Blue nevus | 1 | 1 |
| Compound | 11 | 9 |
| Intradermal | 10 | 7 |
| Junctional | 7 | 6 |
| Lentigo | 7 | 5 |

All cases with complete dermoscopic, clinical, and baseline photographic documentation were included in the study set resulting in 169 lesions from 103 patients (Table I). The grading of uniformity was on the basis of dermoscopic images (digitized images from slides) and the grading of change on digital clinical images taken before excision compared with images cropped from baseline digital total body photos. All identifiable patient information was removed, the order in which the lesions were presented was randomized, and the study set images were assembled into a presentation (Power-Point).

Study Algorithm

The algorithm was developed on the basis of 2 characteristics: nonuniformity and change (specifically, that which was suggestive of growth). "Uniformity" was defined as a grossly consistent gradient of features from the center of the lesion to the edge interfacing with normal skin for the full circumference of the lesion. Biaxial symmetry was not required as long as the gradient of features from the center to the edge was consistent. Lesions not demonstrating these characteristics were considered nonuniform. "Change" was defined as an apparent doubling of area or new lesion, or the development of a new feature that caused concern for the growth of melanoma within a mole; specifically, nonuniform expansion of pigment from one edge of the lesion into adjacent normal skin or the dramatic appearance of new nonuniform pigmentation.

A control set of dermoscopic images was developed to illustrate nonuniform versus uniform lesions and a gross clinical set of images to illustrate changed versus not changed. These images were intended to provide a threshold against which one could compare the unknowns when grading a lesion as nonuniform or changed. These control images were also assembled into a presentation (PowerPoint). The lesions in the control set did not include any lesions from the study set.

The study set of 169 lesions was organized such that for each lesion there was a pair of slides. The first slide was the dermoscopic image for which the reviewer was asked to determine whether the lesion was uniform (yes or no). The second slide in each set included a digital clinical image taken before excision and a cropped baseline digital total body photo of the area. The reviewer was asked to determine whether the lesion had changed (as defined above, yes or no). 3 academic dermatologists participated as reviewers for the study. None of the reviewers had previous exposure to the patients or photographs of their lesions. All reviewers viewed the teaching set before grading the study set. Each reviewer recorded answers on a log sheet. Answers where the reviewer listed the response as equivocal were scored as no. All reviewers completed the study.

Statistical Analysis

The ability to predict melanoma from lesion change and nonuniformity was evaluated with logistic regression analysis. Classification of a lesion as both nonuniform and changed was done in 2 different ways: 2 out of 3 reviewers agreed the lesion was nonuniform and changed, and all 3 reviewers agreed the lesion was nonuniform and changed. Each of these indicator variables was added to a univariate model with melanoma as the outcome of interest and also to a model combining melanoma and dysplastic nevus with severe cytologic atypia as the outcome of interest.

B. Results On the basis of the above-defined definitions of nonuniformity and change, each lesion fell into 1 of 4 categories: (1) nonuniform and changed; (2) uniform and changed; (3) nonuniform and unchanged and; or (4) uniform and unchanged. The breakdown of the individual reviewer responses and the lesion pathology is charted in FIG. 1.

Reviewers 1, 2, and 3 placed 10 of 16, 13 of 16, and 14 of 16 melanomas, respectively, into the category of nonuniform and changed. If agreement of at least 2 of the 3 reviewers is accepted as a positive finding for nonuniformity or change, then 12/16 melanomas were scored positively for both nonuniformity and change (Table II). This included all the superficially invasive tumors. The 4 melanomas not graded as nonuniform and changed were in situ tumors. Of these 4 in situ tumors, 3 of the 4 were graded as changed but uniform. The other tumor was graded differently by each attending; using 2 out of 3 agreement for each variable, its composite grade was nonuniform and not changed.

Using 2 out of 3 reviewer agreement on nonuniformity and change as the predictor variable, the odds ratio (OR) of melanoma for lesions scored as both nonuniform and changed was 4.06 (P=0.0195, 95% confidence interval [CI] 1.25-13.16) times the odds of melanoma for lesions scored otherwise. Using 3 out of 3 agreement, the OR of melanoma for lesions scored as nonuniform and changed was 6 (P=0.0010, 95% CI 2.06-17.52) times the odds of melanoma for lesions scored otherwise.

The present invention is not limited to a particular mechanism. Indeed, an understanding of the mechanism is not necessary to understand the present invention. Nonetheless, it is contemplated that lesions with severe atypia could also include some early malignant lesions that have not yet sufficiently evolved. If the outcome of interest was defined as having severe melanoma or dysplastic nevi with severe atypia, the OR comparing lesions scored as nonuniform and changed with lesions scored otherwise was 2.56 (P=0.0097, 95% CI 1.26-5.25) and 5.08 (P=0.0001, 95% CI 2.30-11.18) for 2 out of 3 and 3 out of 3 agreement, respectively.

The majority of the lesions in the study set were graded as changed (Table II). For the lesions graded as changed (at least 2/3 agreement), there was a clear segregation of the melanomas to the nonuniform subgroup of 80% (12/15). This included 100% (5/5) of the invasive melanomas and 70% (7/10) of the in situ melanomas. To a lesser extent 65% (15/23) of dysplastic nevi with severe atypia also segregated to the nonuniform subgroup. Among the changed benign nevi (dysplastic moderate, mild, and other), there was a relatively even split between those graded as uniform at 48% (47/97) and those graded as nonuniform at 52% (50/97).

TABLE II

Lesion distribution for at least two out of three agreement

| Diagnosis | Nonuniform and changed | Uniform and changed | Nonuniform and not changed | Uniform and not changed | Total |
|---|---|---|---|---|---|
| Melanoma | 12 | 3 | 1 | 0 | 16 |
| Severe | 15 | 8 | 4 | 0 | 27 |
| Other | 50 | 47 | 16 | 13 | 126 |
| Total | 77 | 58 | 21 | 13 | 169 |

This study was based on a highly selected group of lesions for which there was a significant element of concern largely on the basis of clinical features and change noted compared with baseline photos by the clinic physician. No nonuniform and changing lesion was left on a patient. In contrast, nevi not thought to be melanoma on the initial visit and lacking change, even if nonuniform, were not regularly excised. In young adults, there is a high prevalence of newly acquired nevi (Gallagher et al., Dermatol Clin 1995; 13:595-603). These lesions were also not regularly excised unless there was some additional worrisome feature (patient concern, dissimilar from patient's average mole types, or not clearly benign dermoscopic pattern).

Significant ORs were identified for melanoma in the nonuniform and changing group. Of the 16 melanomas in the study, none developed from an obvious dysplastic nevus and, thus, all would have been missed if only dysplastic nevi were being followed up with close-up photos or dermoscopic images. Of the melanomas, 5 evolved from lesions that appeared to be small benign-appearing nevi, 4 evolved in an area where a small pinpoint focus of pigment could be identified, and 7 evolved in skin with no prior identifiable lesion.

The findings described herein confirm that melanomas exhibit growth and eventually display nonuniform dermoscopic features. If all nonuniform and growing lesions are excised during the follow-up of patients at high risk, the data suggest that approximately one third of these lesions would either be melanoma (16%) or dysplastic nevi with severe cytologic atypia (20%). Two thirds would be lesions that may not need to be removed: dysplastic nevi (moderate or mild) and other nevi. This focused approach on only nonuniform and growing lesions would result in less than 0.1 biopsies per patient year (on the basis of clinical experience), yet would result in the detection of 100% of the superficially invasive melanomas and 64% of the in situ melanomas on the basis of this data set.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

I claim:

1. A method, comprising:
   a) providing
      i) at least one initial body image from a subject; and
      ii) at least one follow up body image from said subject, wherein said follow up body image is taken at a later time than said initial body image; and
   b) comparing said initial body image and said follow up body image to identify at least one mole or lesion that
      i) is nonuniform wherein the nonuniformity comprises lacking biaxial symmetry and lacking a consistent gradient of one or more feature from the center of said mole or lesion to the edge of said mole or lesion that interfaces with normal skin for the full circumference of said mole or lesion, wherein said feature is selected from the group consisting of reflectance and absorbance, and
      ii) is changed in said follow up body image compared to said initial body image, wherein the change is selected from the group consisting of
         1) more than 80% increase in surface area, and
         2) detection of a new feature of said mole or lesion, wherein said new feature is selected from
            A) nonuniform expansion of pigment from one edge of said mole or lesion into adjacent normal skin and
            B) inconsistent gradient of pigmentation from the center of said mole or lesion to the edge of said mole or lesion that interfaces with normal skin for the full circumference of said mole or lesion and
         3) is present in said follow up body image and is absent in said initial body image,
wherein said nonuniformity and change are indicative of potential melanoma.

2. The method of claim 1, further comprising the step of providing a diagnosis of the presence or absence of melanoma in said subject.

3. The method of claim 1, wherein said moles or lesions that are both nonuniform and changed are indicative of dysplastic nevus with severe cytologic atypia.

4. The method of claim 1, further comprising the step of determining a level of risk of melanoma being present in said subject.

5. The method of claim 1, wherein said at least one follow up body image is taken repeatedly at regular or irregular intervals.

6. The method of claim 5, wherein said intervals range from once every 3 months to once every 24 months.

7. The method of claim 1, further comprising providing at least one initial dermoscopy image and at least one follow up dermoscopy image.

8. The method of claim 7, further comprising comparing said at least one initial dermoscopy image and said at least one follow up dermoscopy image to identify moles that are both nonuniform and changed.

9. The method of claim 1, wherein said initial and follow up body image are compared by at least one dermatologist.

10. The method of claim 1, wherein said initial and follow up body image are compared by a computer processor and computer software.

11. The method of claim 10, wherein said computer software and said computer processor provide a diagnosis of the presence or absence of melanoma to said subject.

12. The method of claim 10, wherein said computer software and said computer processor provide an indication of a level of risk for the development of melanoma to said subject.

13. The method of claim 1, wherein said body images are 3-dimensional.

14. The method of claim 1, further comprising the step of excising said moles found to be both nonuniform and changed.

15. The method of claim 1, further comprising providing a set of control body images, wherein said control body images illustrate changed and nonchanged as well as uniform and nonuniform moles or lesions.

16. A method, comprising:
a) providing
  i) at least one initial body image from a subject; and
  ii) at least one follow up body image from said subject, wherein said follow up body image is taken at a later time than said initial body image; and
b) comparing said initial body image and said follow up body image to identify at least one mole or lesion that
  i) is nonuniform, wherein the nonuniformity comprises lacking biaxial symmetry and lacking a consistent gradient of reflectance, absorbance, color, and color intensity from the center of said mole or lesion to the edge of said mole or lesion that interfaces with normal skin for the full circumference of said mole or lesion, and
  ii) is changed in said follow up body image compared to said initial body image, wherein the change comprises
    1) more than 80% increase in surface area, and
    2) detection of
      A) new nonuniform expansion of pigment from one edge of said mole or lesion into adjacent normal skin, and
      B) new inconsistent gradient of pigmentation from the center of said mole or lesion to the edge of said mole or lesion that interfaces with normal skin for the full circumference of said mole or lesion, wherein said nonuniformity and change are indicative of potential melanoma.

17. The method of claim 16, further comprising the step of providing a diagnosis of the presence or absence of melanoma in said subject.

18. The method of claim 16, wherein said moles or lesions that are both nonuniform and changed are indicative of dysplastic nevus with severe cytologic atypia.

19. The method of claim 16, further comprising the step of determining a level of risk of melanoma being present in said subject.

20. The method of claim 16, wherein said at least one follow up body image is taken repeatedly at regular or irregular intervals.

21. The method of claim 20, wherein said intervals range from once every 3 months to once every 24 months.

22. The method of claim 16, further comprising providing at least one initial dermoscopy image and at least one follow up dermoscopy image.

23. The method of claim 22, further comprising comparing said at least one initial dermoscopy image and said at least one follow up dermoscopy image to identify moles that are both nonuniform and changed.

24. The method of claim 16, wherein said initial and follow up body image are compared by at least one dermatologist.

25. The method of claim 16, wherein said initial and follow up body image are compared by a computer processor and computer software.

26. The method of claim 25, wherein said computer software and said computer processor provide a diagnosis of the presence or absence of melanoma to said subject.

27. The method of claim 25, wherein said computer software and said computer processor provide an indication of a level of risk for the development of melanoma to said subject.

28. The method of claim 16, wherein said body images are 3-dimensional.

29. The method of claim 16, further comprising the step of excising said moles found to be both nonuniform and changed.

30. The method of claim 16, further comprising providing a set of control body images, wherein said control body images illustrate changed and nonchanged as well as uniform and nonuniform moles or lesions.

\* \* \* \* \*